(12) United States Patent
Lee

(10) Patent No.: US 11,883,072 B2
(45) Date of Patent: Jan. 30, 2024

(54) MEDICAL DEVICE

(71) Applicant: FINE MEDIX CO., LTD., Dong-gu (KR)

(72) Inventor: Tae Gyung Lee, Michuhol-gu (KR)

(73) Assignee: FINE MEDIX CO., LTD, Daegu (KR)

( * ) Notice: Subject to any disclaimer, the term of this patent is extended or adjusted under 35 U.S.C. 154(b) by 891 days.

(21) Appl. No.: 16/764,620

(22) PCT Filed: Jun. 18, 2019

(86) PCT No.: PCT/KR2019/007297
§ 371 (c)(1),
(2) Date: May 15, 2020

(87) PCT Pub. No.: WO2020/105828
PCT Pub. Date: May 28, 2020

(65) Prior Publication Data
US 2020/0289158 A1    Sep. 17, 2020

(30) Foreign Application Priority Data

Nov. 22, 2018 (KR) .......................... 10-2018-0145042

(51) Int. Cl.
*A61B 17/34* (2006.01)
*A61B 17/3211* (2006.01)
(Continued)

(52) U.S. Cl.
CPC ...... *A61B 17/3478* (2013.01); *A61B 10/0283* (2013.01); *A61B 10/04* (2013.01);
(Continued)

(58) Field of Classification Search
CPC ........ A61B 17/3478; A61B 17/320016; A61B 17/3494; A61B 2010/045;
(Continued)

(56) References Cited

U.S. PATENT DOCUMENTS 5,766,184 A    6/1998  Matsuno
6,010,627 A *  1/2000  Hood, III ............... A61K 35/14
                                              210/321.89
(Continued)

FOREIGN PATENT DOCUMENTS

JP    2012517860 A    8/2012
JP    2016104205 A    6/2016
(Continued)

OTHER PUBLICATIONS

Office Action issued in connection with corresponding European Application No. 19886038.9-1122 dated Jun. 22, 2022.

*Primary Examiner* — James D Ponton
*Assistant Examiner* — Neeraja Gollamudi
(74) *Attorney, Agent, or Firm* — TAROLLI, SUNDHEIM, COVELL & TUMMINO L.L.P.

(57) ABSTRACT

A medical device is provided that includes a fine needle aspiration device and an incision device, which are inserted into a body with an endoscope. The fine needle aspiration device includes an injection needle and an injection needle tube, which surrounds the injection needle. A first limiting unit limits the length of the needlepoint of the injection needle protruding from the injection needle tube. A syringe is connected to the injection needle for tissue collection and medicine injection. A second limiting unit limits the connection between the injection needle and the syringe. The incision device includes a knife and a knife tube that surrounds the knife. A third limiting unit limits the length of the cutting edge of the knife protruding from the knife tube.

14 Claims, 8 Drawing Sheets

(51) Int. Cl.
    *A61B 17/32*     (2006.01)
    *A61M 1/00*     (2006.01)
    *A61M 5/142*     (2006.01)
    *A61M 5/145*     (2006.01)
    *A61B 10/02*     (2006.01)
    *A61B 10/04*     (2006.01)
    *A61B 17/00*     (2006.01)
    *A61B 90/00*     (2016.01)
    *A61M 5/158*     (2006.01)

(52) U.S. Cl.
    CPC .... *A61B 17/00234* (2013.01); *A61B 17/3211* (2013.01); *A61B 17/320016* (2013.01); *A61B 17/3403* (2013.01); *A61B 17/3494* (2013.01); *A61M 1/85* (2021.05); *A61M 1/87* (2021.05); *A61M 5/1452* (2013.01); *A61M 5/14212* (2013.01); *A61B 2010/045* (2013.01); *A61B 2017/0034* (2013.01); *A61B 2017/00296* (2013.01); *A61B 2017/320052* (2013.01); *A61B 2090/034* (2016.02); *A61B 2090/08021* (2016.02); *A61M 2005/1588* (2013.01)

(58) Field of Classification Search
    CPC .. A61B 2017/0034; A61B 2017/32113; A61B 17/3211; A61M 1/85; A61M 1/87; A61M 5/14212; A61M 5/1452; A61M 2005/1588
    See application file for complete search history.

(56) References Cited

U.S. PATENT DOCUMENTS

| | | | |
|---|---|---|---|
| 2008/0306334 A1* | 12/2008 | Okada | A61B 18/1492 30/151 |
| 2009/0062830 A1 | 3/2009 | Hiraoka | |
| 2010/0217151 A1* | 8/2010 | Gostout | A61B 17/320783 600/564 |
| 2016/0242803 A1 | 8/2016 | Shin et al. | |

FOREIGN PATENT DOCUMENTS

| | | |
|---|---|---|
| KR | 20070041784 A | 4/2007 |
| KR | 100943130 B1 | 2/2012 |
| WO | 2016002835 A1 | 1/2016 |

\* cited by examiner

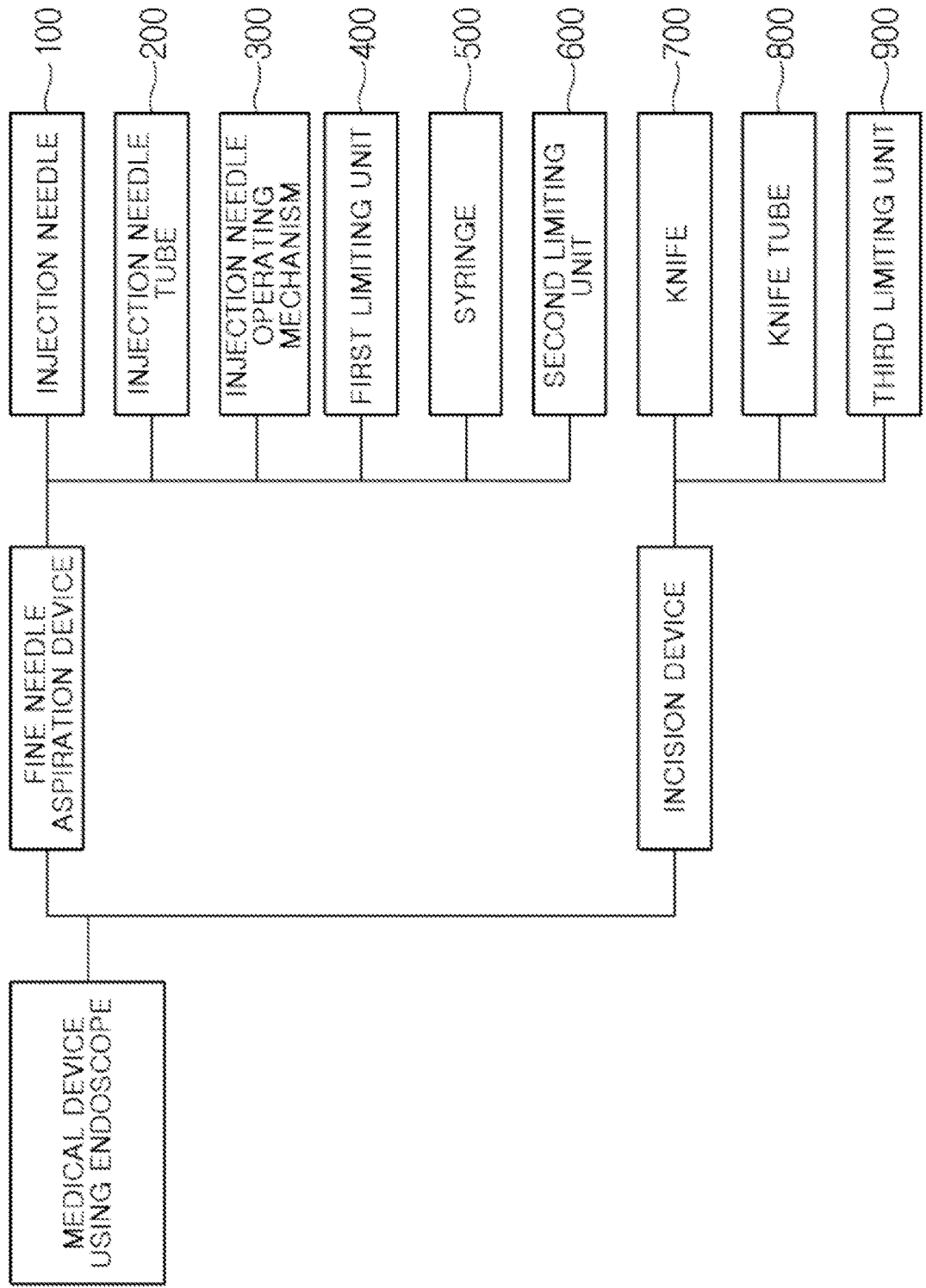
[FIG. 1]

[FIG. 2]
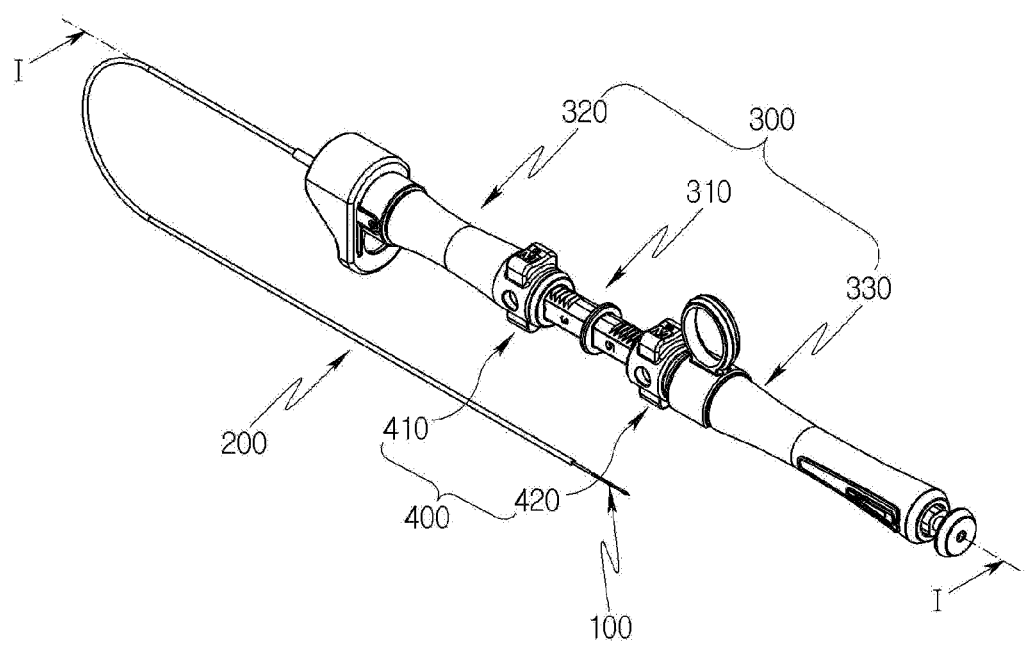

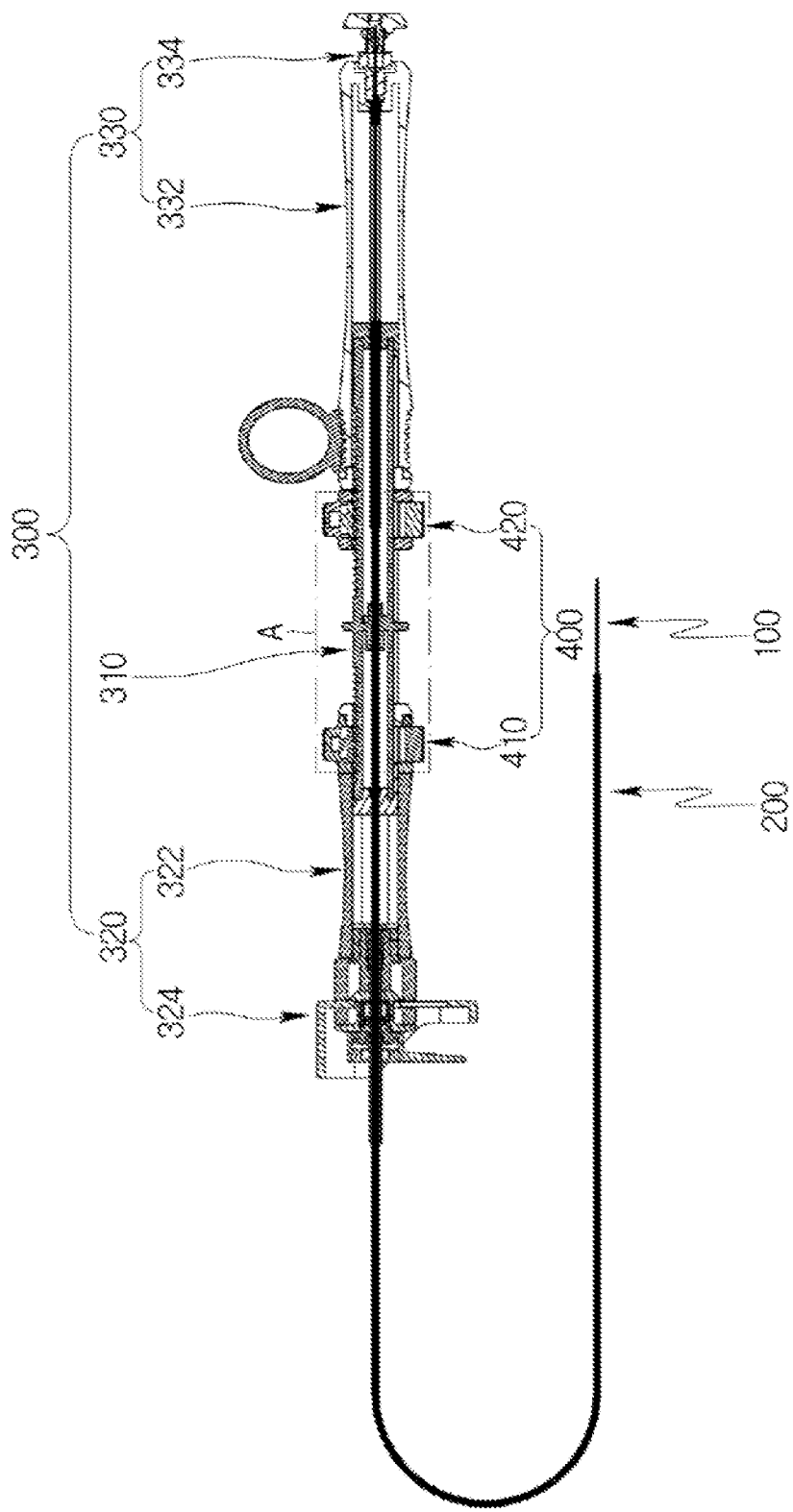
[FIG. 3]

[FIG. 4]
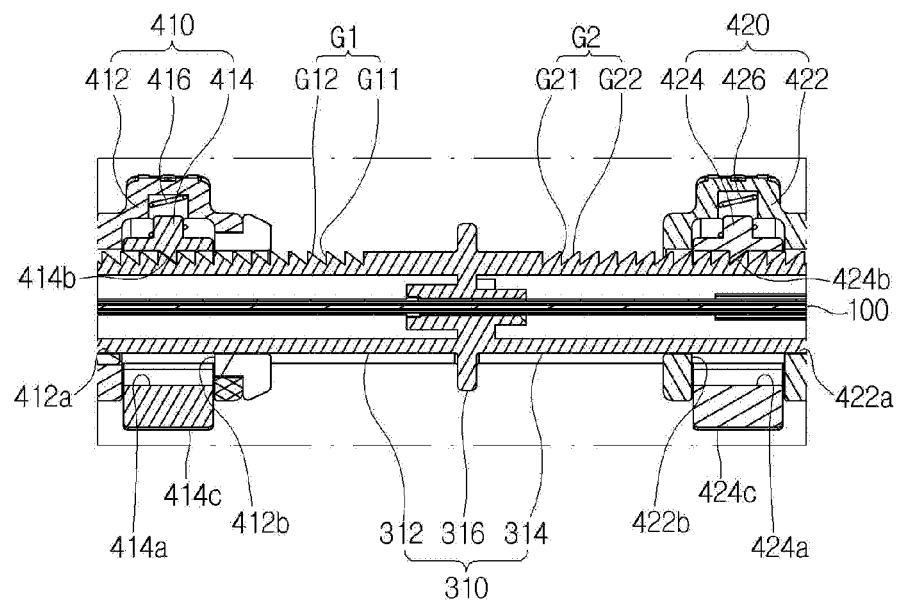
[FIG. 5]
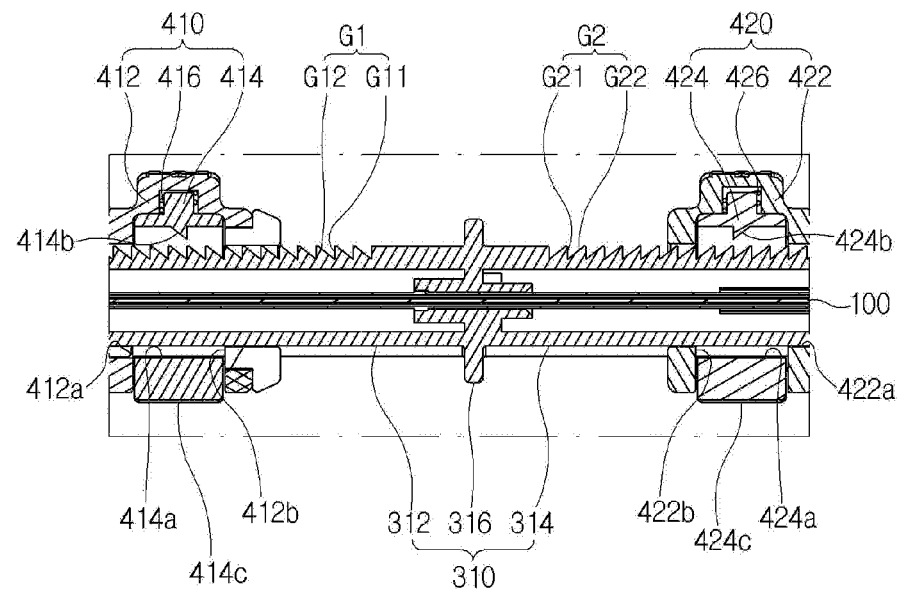

[FIG. 6]
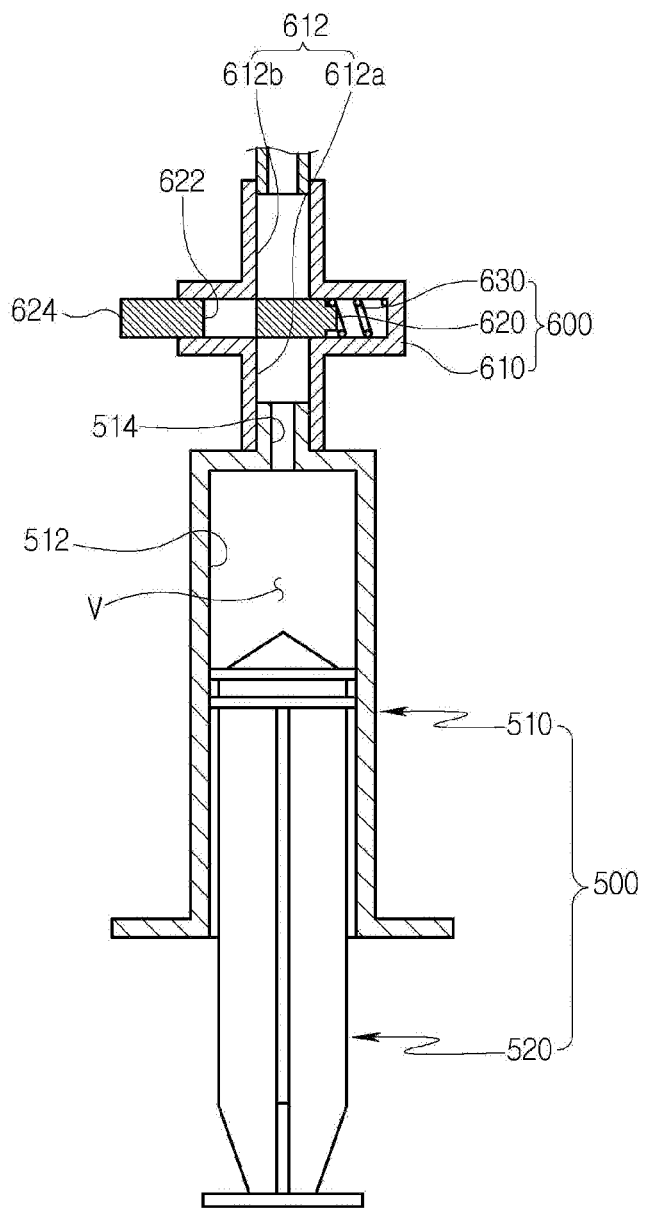

[FIG. 7]
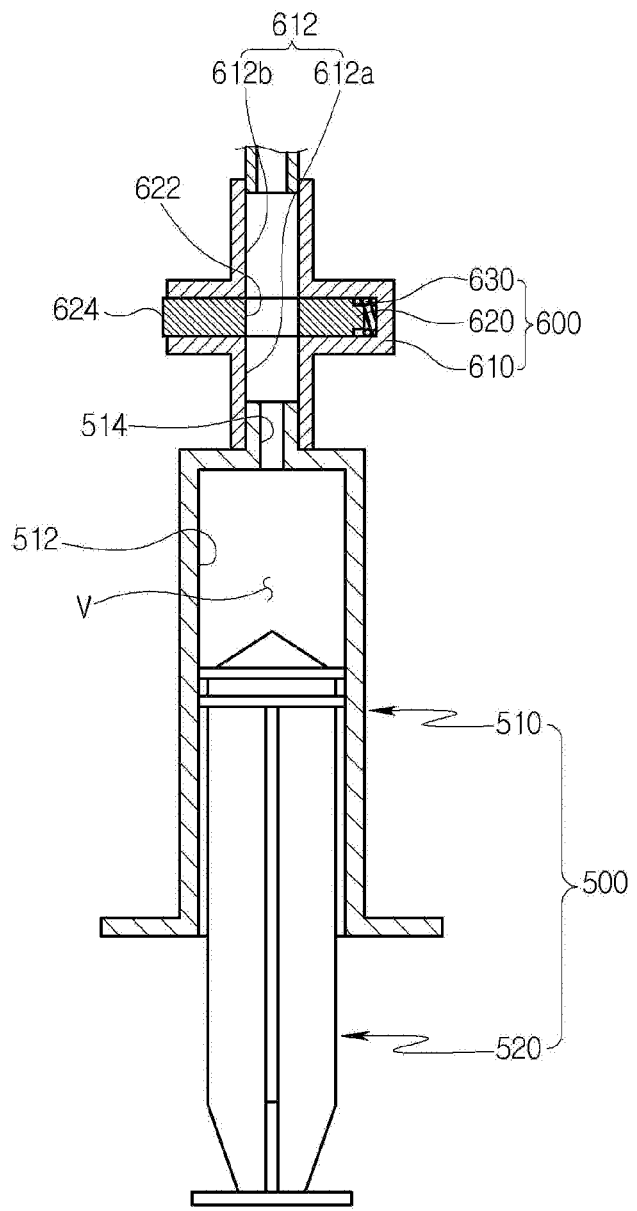

[FIG. 8]
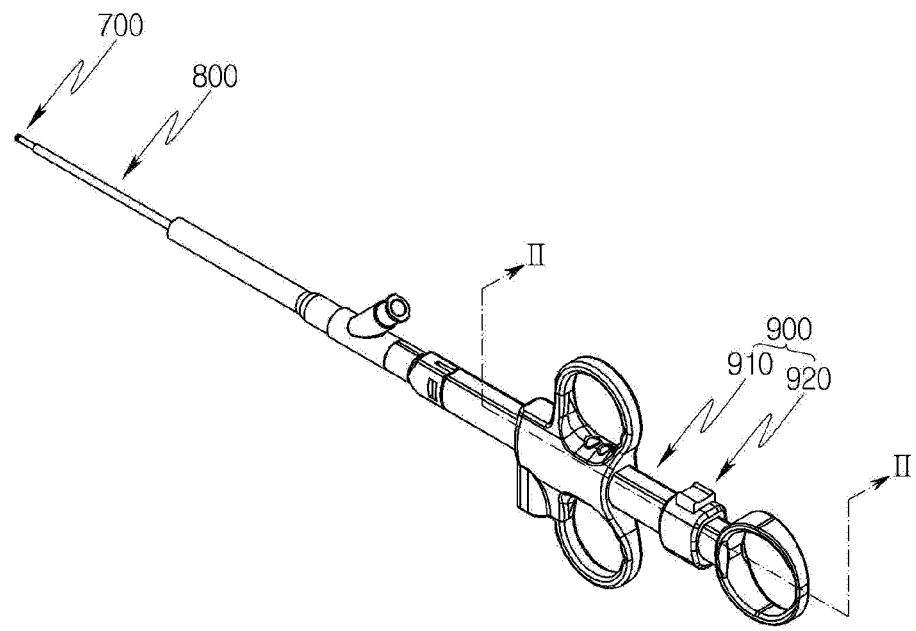
[FIG. 9]
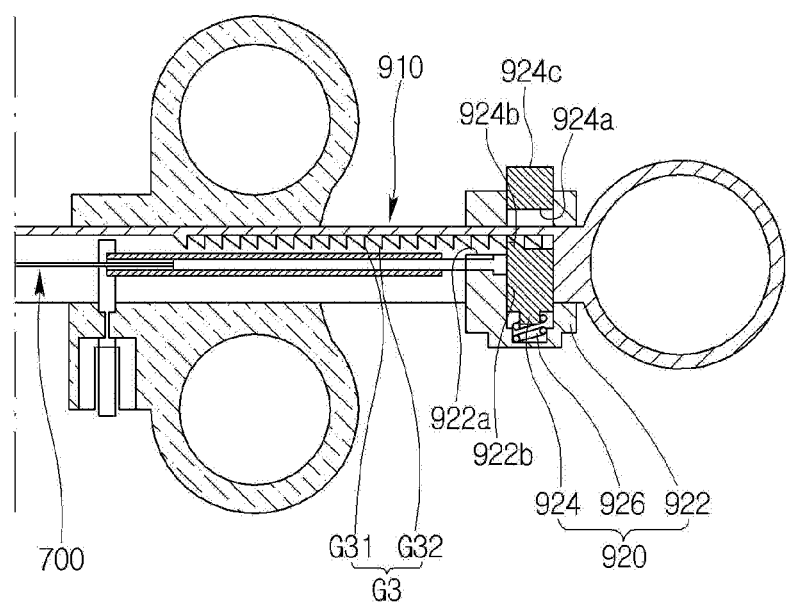

[FIG. 10]
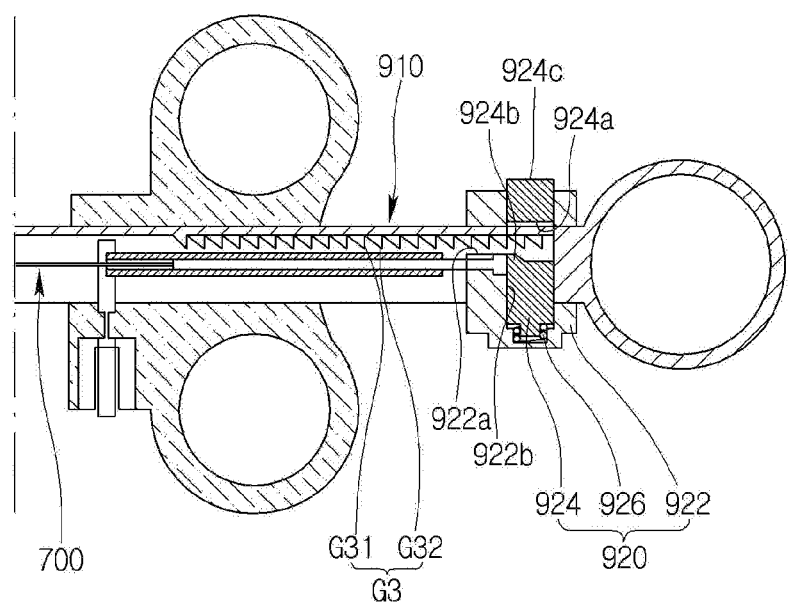

MEDICAL DEVICE

RELATED APPLICATIONS

The present invention is a U.S. National Stage under 35 USC 371 patent application, claiming priority to Serial No. PCT/KR2019/007297, filed on 18 Jun. 2019; which claims priority of KR 10 2018 0145042, filed on 22 Nov. 2018, the entirety of both of which are incorporated herein by reference.

TECHNICAL FIELD

The present disclosure relates to a medical device, and more particularly, to a medical device which is inserted into the body by using an endoscope to perform the treatment such as tissue collection or medicine injection.

BACKGROUND ART

Generally, a medical endoscope (hereinafter, referred to as an endoscope) is inserted into a body so that the inside of the body may be seen, and recently, a medical device which is inserted into the body by using an endoscope for the treatment such as tissue collection or medicine injection has been disclosed, and such a medical device includes a fine needle aspiration device and an incision device.

Japanese Patent Laid-Open Publication No. 2013-538099 discloses the fine needle aspiration device including an injection needle, an injection needle tube which surrounds the injection needle, and an injection needle operating mechanism which moves the injection needle so that the needlepoint of the injection needle protrudes from the injection needle tube or is inserted into the injection needle tube.

Korean Patent No. 10-1717287 discloses a cock which communicates and shields the injection needle and a syringe of the fine needle aspiration device.

Korean Patent No. 10-1310371 discloses an incision device including a knife for cutting a surgical site, a knife tube which surrounds the knife, and a knife operating mechanism which moves the knife so that the cutting edge of the knife protrudes from the knife tube or is inserted into the knife tube.

However, such a conventional medical device has a problem in that an operation is inconvenient.

Specifically, the fine needle aspiration device disclosed in Japanese Patent Laid-Open Publication No. 2013-538099 includes a stopper which limits the length of the needlepoint of the injection needle protruding from the injection needle tube, and as the stopper is formed in a bolt manner, an operator is required to rotate the bolt in one direction to fix the stopper, and the operator is required to rotate the bolt in the opposite direction to release the stopper. Accordingly, there is a problem in that the operation of the stopper is cumbersome, and the time required for operating the stopper is increased.

Further, the cock disclosed in Korean Patent No. 10-1717287 includes a valve which opens and closes the passage between the injection needle and the syringe, and as the valve is formed in a rotating manner, the operator is required to rotate the valve in one direction to open the passage between the injection needle and the syringe, and the operator is required to rotate the valve in the opposite direction to close the passage between the injection needle and the syringe. Accordingly, there is a problem in that the operation of the cock is cumbersome, and the time required for operating the cock is increased.

Further, the incision device disclosed in Korean Patent No. 10-1310371 includes the stopper which limits the length of the cutting edge of the knife protruding from the knife tube, and as the stopper is formed in a bolt manner, the operator is required to rotate the bolt in one direction to fix the stopper, and the operator is required to rotate the bolt in the opposite direction to release the stopper. Accordingly, there is a problem in that the operation of the stopper is cumbersome, and the time required for operating the stopper is increased.

DISCLOSURE

Technical Problem

Accordingly, an object of the present disclosure is to provide a medical device capable of performing an operation simply.

Technical Solution

For achieving the object, the present disclosure includes a medical device which includes a fine needle aspiration device and an incision device which are inserted into a body by using an endoscope, and the fine needle aspiration device includes: an injection needle which is injected into a surgical site; an injection needle tube which surrounds the injection needle; a first limiting unit which limits the length of the needlepoint of the injection needle protruding from the injection needle tube; a syringe which is connected to the injection needle for tissue collection and medicine injection; and a second limiting unit which limits the connection between the injection needle and the syringe, the incision device includes: a knife configured to cut the surgical site; a knife tube which surrounds the knife; and a third limiting unit which limits the length of the cutting edge of the knife protruding from the knife tube, and at least one of the first limiting unit, the second limiting unit, and the third limiting unit is formed so that the limiting function is released when an external force is applied by an operator and the limiting function is restored when the external force is removed.

The fine needle aspiration device may further include an injection needle operating mechanism which moves the injection needle so that the needlepoint of the injection needle protrudes from the injection needle tube or is inserted into the injection needle tube, the injection needle operating mechanism may include an injection needle guide part which extends in one direction; a first gripping part which is coupled to the injection needle tube and is movable along a first injection needle guide part which is one end of the injection needle guide part; and a second gripping part which is coupled to the injection needle and is movable along a second injection needle guide part which is the other end of the injection needle guide part, and the first limiting unit may include a first stopper which fixes the first gripping part to the injection needle guide part; and a second stopper which prevents the second gripping part from being closer to the first gripping part than a predetermined position.

The first stopper may include a first housing which has a first through hole formed to penetrate in one direction and a first intersecting hole intersecting with the first through hole and is formed integrally with the first gripping part; a first core which is provided to be reciprocable in a first direction and a second direction which is the opposite direction of the first direction along the first intersecting hole and has a first communicating hole which is communicable with the first through hole; and a first spring which applies an elastic force to the first core in the second direction, and the first injection needle guide part may be inserted into the first through hole and the first communicating hole.

The first injection needle guide part may be formed with a plurality of first grooves along the extending direction of the injection needle guide part, the first core may include a first protrusion which protrudes from the first communicating hole and is insertable into any one of the plurality of first grooves and a first exposing part which is exposed to the outside of the first intersecting hole; when an external force is applied to the first exposing part, the first core may move in the first direction by the external force, and the first protrusion may be drawn out from the plurality of first grooves, such that the first gripping part and the first stopper are movable along the first injection needle guide part; and when the external force is removed, the first core moves in the second direction by the first spring, and the first protrusion is inserted into any one of the plurality of first grooves, such that the first gripping part and the first stopper may be fixed to the injection needle guide part.

The first groove may include a first groove first support surface which supports the first protrusion at the second gripping part side with respect to the first protrusion; and a first groove second support surface which supports the first protrusion at the opposite side of the first groove first support surface with respect to the first protrusion, the first groove first support surface may be formed perpendicular to the extending direction of the injection needle guide part, and the first groove second support surface may be formed to be inclined to the extending direction of the injection needle guide part so as to push the first protrusion to the outside of the first groove as the first groove second support surface moves away from the second gripping part.

The second stopper may include a second housing which has a second through hole formed to penetrate in one direction and a second intersecting hole intersecting with the second through hole and is provided between the first gripping part and the second gripping part; a second core which is provided to be reciprocable in a third direction and a fourth direction which is the opposite direction of the third direction along the second intersecting hole and has a second communication hole which is communicable with the second through hole; and a second spring which applies an elastic force to the second core in the fourth direction, and the second injection needle guide part may be inserted into the second through hole and the second communicating hole.

The second injection needle guide part may be formed with a plurality of second grooves along the extending direction of the injection needle guide part, the second core may include a second protrusion which protrudes from the second communicating hole and is insertable into any one of the plurality of second grooves and a second exposing part which is exposed to the outside of the second intersecting hole; when the external force is applied to the second exposing part, the second core moves in the third direction by the external force, and the second protrusion is drawn out from the plurality of second grooves, such that the second stopper is movable along the second injection needle guide part; and when the external force is removed, the second core moves in the fourth direction by the second spring, and the second protrusion is inserted into any one of the plurality of second grooves, such that the second stopper may be fixed to the injection needle guide part.

The second gripping part is movable along the second injection needle guide part separately from the second stopper, and the second gripping part may move toward the first gripping part and then may be blocked by the second stopper, thereby preventing the second gripping part from being closer to the first gripping part than a predetermined position.

The second groove may include a second groove first support surface which supports the second protrusion at the first gripping part side with respect to the second protrusion; and a second groove second support surface which supports the second protrusion at the opposite side of the second groove first support surface with respect to the second protrusion; the second groove first support surface may be formed perpendicular to the extending direction of the injection needle guide part; and the second groove second support surface may be formed to be inclined to the extending direction of the injection needle guide part so as to push the second protrusion to the outside of the second groove as the second groove second support surface moves away from the first gripping part.

The third limiting unit may include a knife guide part which is coupled to the knife tube and extends in one direction; and a third stopper which is coupled to the knife, is movable along the knife guide part, and is fixed to the knife guide part when being positioned at a predetermined position.

The third stopper may include a third housing which has a third through hole formed to penetrate in one direction and a third intersecting hole intersecting with the third through hole and is coupled to the knife; a third core which is provided to be reciprocable in a fifth direction and a sixth direction which is the opposite direction of the fifth direction along the third intersecting hole and has a third communicating hole which is communicable with the third through hole; and a third spring which applies an elastic force to the third core in the sixth direction, and the knife guide part may be inserted into the third through hole and the third communicating hole.

The knife guide part may be formed with a plurality of third grooves along the extending direction of the knife guide part; the third core may include a third protrusion which protrudes from the third communicating hole and is insertable into any one of the plurality of third grooves and a third exposing part which is exposed to the outside of the third intersecting hole; when the external force is applied to the third exposing part, the third core moves in the fifth direction by the external force, and the third protrusion is drawn out from the plurality of third grooves, such that the third stopper is movable along the knife guide part; and when the external force is removed, the third core moves in the sixth direction by the third spring, and the third protrusion is inserted into any one of the plurality of third grooves, such that the third stopper may be fixed to the knife guide part.

The third groove may include a third groove first support surface which supports the third protrusion at the knife side with respect to the third protrusion; and a third groove second support surface which supports the third protrusion at the opposite side of the third groove first support surface with respect to the third protrusion; the third groove first support surface may be formed perpendicular to the extending direction of the knife guide part; and the third groove second support surface may be formed to be inclined to the extending direction of the knife guide part so as to push the third protrusion to the outside of the third groove as the third groove second support surface moves away from the knife.

The syringe may include a hollow barrel which has a bore; and a plunger which reciprocates along the bore; the second limiting unit may include a fourth housing which has a fourth through hole formed to penetrate in one direction and a fourth intersecting hole intersecting with the fourth through hole; a fourth core which is provided to be reciprocable in a seventh direction and an eighth direction which is the opposite direction of the seventh direction along the fourth intersecting hole and has a fourth communicating hole which is communicable with the fourth through hole; and a fourth spring which applies an elastic force to the fourth core in the eighth direction; and one end of the fourth through hole may communicate with the syringe, and the other end of the fourth through hole may communicate with the injection needle.

The fourth core may include a fourth exposing part which is exposed to the outside of the fourth intersecting hole; when the external force is applied to the fourth exposing part, the fourth core moves in the seventh direction by the external force and the fourth communicating hole communicates with the fourth through hole, such that the syringe may communicate with the injection needle through the fourth through hole and the fourth communicating hole; and when the external force is removed, the fourth core moves in the eighth direction by the fourth spring, and the fourth communicating hole is shielded from the fourth through hole, thereby blocking the communication between the syringe and the injection needle.

Advantageous Effects

The medical device according to the present disclosure includes the fine needle aspiration device and the incision device which are inserted into the body by using the endoscope; the fine needle aspiration device includes the injection needle; the injection needle tube which surrounds the injection needle; the first limiting unit which limits the length of the needlepoint of the injection needle protruding from the injection needle tube; the syringe which is connected to the injection needle for tissue collection and medicine injection; and the second limiting unit which limits the connection between the injection needle and the syringe; the incision device includes the knife; the knife tube which surrounds the knife; and the third limiting unit which limits the length of the cutting edge of the knife protruding from the knife tube; and at least one of the first limiting unit, the second limiting unit, and the third limiting unit is formed so that the limiting function is released when an external force is applied by the operator and the limiting function is restored when the external force is removed, thereby performing the operation simply.

DESCRIPTION OF DRAWINGS

FIG. 1 is a system diagram illustrating a medical device according to an exemplary embodiment of the present disclosure.

FIG. 2 is a perspective diagram illustrating an injection needle, tube, injection needle operating mechanism, and first limiting unit of a fine needle aspiration device in the medical device illustrated in FIG. 1.

FIG. 3 is a cross-sectional diagram taken along the line I-I of FIG. 2.

FIG. 4 is an enlarged diagram of a portion A of FIG. 3.

FIG. 5 is a cross-sectional diagram illustrating a state where the limiting function of the first limiting unit illustrated in FIG. 4 is released.

FIG. 6 is a cross-sectional diagram illustrating a syringe and a second limiting unit of the fine needle aspiration device in the medical device illustrated in FIG. 1.

FIG. 7 is a cross-sectional diagram illustrating a state where the limiting function of the second limiting unit illustrated in FIG. 6 is released.

FIG. 8 is a perspective diagram illustrating an incision device and a third limiting unit in the medical device illustrated in FIG. 1.

FIG. 9 is a cross-sectional diagram taken along the line II-II of FIG. 8.

FIG. 10 is a cross-sectional diagram illustrating a state where the limiting function of the third limiting unit illustrated in FIG. 9 is released.

BEST MODE

Hereinafter, a medical device according to the present disclosure will be described in detail with reference to the accompanying drawings.

FIG. 1 is a system diagram illustrating a medical device according to an exemplary embodiment of the present disclosure, FIG. 2 is a perspective diagram illustrating an injection needle, tube, injection needle operating mechanism, and first limiting unit of a fine needle aspiration device in the medical device illustrated in FIG. 1, FIG. 3 is a cross-sectional diagram taken along the line I-I of FIG. 2, FIG. 4 is an enlarged diagram of a portion A of FIG. 3, FIG. 5 is a cross-sectional diagram illustrating a state where the limiting function of the first limiting unit illustrated in FIG. 4 is released, FIG. 6 is a cross-sectional diagram illustrating a syringe and a second limiting unit of the fine needle aspiration device in the medical device illustrated in FIG. 1, FIG. 7 is a cross-sectional diagram illustrating a state where the limiting function of the second limiting unit illustrated in FIG. 6 is released, FIG. 8 is a perspective diagram illustrating an incision device and a third limiting unit in the medical device illustrated in FIG. 1, FIG. 9 is a cross-sectional diagram taken along the line II-II of FIG. 8, and FIG. 10 is a cross-sectional diagram illustrating a state where the limiting function of the third limiting unit illustrated in FIG. 9 is released.

Referring to FIG. 1, a medical device according to an exemplary embodiment of the present disclosure may include a fine needle aspiration device which is inserted into a body by using an endoscope.

The fine needle aspiration device may include an injection needle 100 which is injected into a surgical site, an injection needle tube 200 which surrounds the injection needle 100 to protect the injection needle 100, an injection needle operating mechanism 300 which moves the injection needle 100 so that the needlepoint of the injection needle 100 protrudes from the injection needle tube 200 or is inserted into the injection needle tube 200, a first limiting unit 400 which limits the length of the needlepoint of the injection needle 100 protruding from the injection needle tube 200, a syringe 500 which is connected to the injection needle 100 for tissue collection and medicine injection, and a second limiting unit 600 which limits the connection between the injection needle 100 and the syringe 500.

First, referring to FIGS. 2 to 5, the injection needle 100, the injection needle tube 200, the injection needle operating mechanism 300, and the first limiting unit 400 according to the present exemplary embodiment will be described.

That is, the injection needle 100 is formed of a hollow tube, and the needlepoint of the injection needle 100 is obliquely cut, such that a portion of the circumference of the injection needle 100 may be formed to be stood up.

Further, an injection hole which communicates the inside and the outside of the injection needle 100 may be formed on the cut surface of the needlepoint thereof.

The injection needle tube 200 may be formed of a hollow tube in which the inner diameter of the injection needle tube 200 is larger than or equal to the outer diameter of the injection needle 100.

Further, the injection needle tube 200 may have one end of the injection needle tube 200 coupled to a first gripping part 320 to be described later, and may be fixed to the first gripping part 320 even if the injection needle 100 moves.

The injection needle operating mechanism 300 may include an injection needle guide part 310 which extends in one direction, the first gripping part 320 which is coupled to the injection needle tube 200 and is movable along a first injection needle guide part 312 which is one end of the injection needle guide part 310 and a second gripping part 330 which is coupled to the injection needle 100 and is movable along a second injection needle guide part 314 which is the other end of the injection needle guide part 310.

The inject needle guide part 310 may include the first injection needle guide part 312 which guides the movement of the first gripping part 320, the second injection needle guide part 314 which guides the movement of the second gripping part 330, and a stepped part 316 which is interposed between the first injection needle guide part 312 and the second injection needle guide part 314.

The first injection needle guide part 312 may be formed to extend in one direction from the stepped part 316, may be inserted into the first gripping part 320, and may be formed to be movable relatively to the first gripping part 320.

A first groove (G1), into which a first protrusion 414*b* of a first core 414 to be described later is inserted, may be formed in the outer circumferential surface of the first injection needle guide part 312.

A plurality of first grooves (G1) may be formed, and the plurality of first grooves (G1) may be arranged at regular intervals along the extending direction of the first injection needle guide part 312.

Further, each of the plurality of first grooves (G1) may include a first groove first support surface (G11) which supports the first protrusion 414*b* to be described later at the second gripping part 330 side with respect to the first protrusion 414*b* to be described later and a first groove second support surface (G12) which supports the first protrusion 414*b* to be described later at the opposite side of the first groove first support surface (G11) with respect to the first protrusion 414*b* to be described later.

The first groove first support surface (G11) may be formed perpendicular to the extending direction of the first injection needle guide part 312.

The first groove second support surface (G12) may be formed to be inclined to the extending direction of the first injection needle guide part 312. That is, the first groove second support surface (G12) may be formed to push the first protrusion 414*b* to be described later to the outside of the first groove (G1) as the first groove second support surface (G12) moves away from the second gripping part 330.

The second injection needle guide part 314 may be formed to extend in a direction opposite to the extending direction of the first injection needle guide part 312 from the stepped part 316, may be inserted into the second gripping part 330, and may be formed to be movable relatively to the second gripping part 330.

A second groove (G2), into which a second protrusion 424*b* of a second core 424 to be described later is inserted, may be formed in the outer circumferential surface of the second injection needle guide part 314.

A plurality of second grooves (G2) may be formed, and the plurality of second grooves (G2) may be arranged at regular intervals along the extending direction of the second injection needle guide part 314.

Further, each of the plurality of second grooves (G2) may include a second groove first support surface (G21) which supports the second protrusion 424*b* to be described later at the first gripping part 320 side with respect to the second protrusion 424*b* to be described later and a second groove second support surface (G22) which supports the second protrusion 424*b* to be described later at the opposite side of the second groove first support surface (G21) with respect to the second protrusion 424*b* to be described later.

The second groove first support surface (G21) may be formed perpendicular to the extending direction of the second injection needle guide part 314.

The second groove second support surface (G22) may be formed to be inclined to the extending direction of the second injection needle guide part 314. That is, the second groove second support surface (G22) may be formed to push the second protrusion 424*b* to be described later to the outside of the second groove (G2) as the second groove second support surface (G22) moves away from the first gripping part 320.

The stepped part 316 may be formed so that the outer diameter of the stepped part 316 is larger than the outer diameter of the first injection needle guide part 312 and the outer diameter of the second injection needle guide part 314.

Meanwhile, the injection needle guide part 310 may be formed of a hollow tube so that the injection needle 100 penetrates the inside of the injection needle guide part 310 (more accurately, the first injection needle guide part 312, the stepped part 316, and the second injection needle guide part 314).

The first gripping part 320 may include a first handle 322 which is movable relatively to the first injection needle guide part 312 and an injection needle tube support part 324 configured to fix the injection needle tube 200 to the first handle 322.

The first handle 322 may be formed of a hollow tube extending in one direction so that the first injection needle guide part 312 may be inserted into the first handle 322.

The injection needle tube support part 324 may be fastened to the end of the first handle 322, and fastened to the injection needle tube 200.

The second gripping part 330 may include a second handle 332 which is movable relatively to the second injection needle guide part 314 and an injection needle support part 334 configured to fix the injection needle 100 to the second handle 332.

The second handle 332 may be formed of a hollow tube extending in one direction so that the second injection needle guide part 314 may be inserted into the second handle 332.

The injection needle support part 334 may be fastened to the end of the second handle 332, and fastened to the injection needle 100.

Further, the injection needle support part 334 may be formed to communicate the injection needle 100 with a pipe (P) to be described later.

The first limiting unit 400 may include a first stopper 410 which fixes the first gripping part 320 to the injection needle guide part 310 and a second stopper 420 which prevents the second gripping part 330 from being closer to the first gripping part 320 than a predetermined position.

The first stopper 410 is interposed between the first gripping part 320 and the stepped part 316, and may include a first housing 412 which is formed integrally with the first gripping part 320, the first core 414 which is formed to be reciprocable in the first housing 412, and a first spring 416 which applies an elastic force to the first core 414.

The first housing 412 may include a first through hole 412a which is formed to penetrate in one direction and a first intersecting hole 412b which intersects with the first through hole 412a.

The first core 414 may be formed to be reciprocable in a first direction and a second direction which is the opposite direction of the first direction along the first intersecting hole 412b.

Further, the first core 414 may include a first communicating hole 414a which is communicable with the first through hole 412a, a first protrusion 414b which protrudes from the first communicating hole 414a and is insertable into any one of the plurality of first grooves (G1), and a first exposing part 414c which is exposed to the outside of the first intersecting hole 412b.

The first spring 416 may be formed of a coil spring which applies an elastic force to the first core 414 in the second direction.

Here, the first injection needle guide part 312 is inserted into the first through hole 412a and the first communicating hole 414a, and in this state, in order for the first stopper 410 to be movable along the first injection needle guide part 312 together with the first gripping part 320, and for the first core 414 to be movable along the first intersecting hole 412b, the first through hole 412a may be formed of a substantially circular hole in which the inner diameter of the first through hole 412a is substantially equal to the outer diameter of the first injection needle guide part 312, and the first communicating hole 414a may be formed of a long hole-shaped hole in which the length of the short axis is substantially equal to the outer diameter of the first injection needle guide part 312 and the length of the long axis is larger than the outer diameter of the first injection needle guide part 312.

Further, the first protrusion 414b may be formed to correspond to the first groove (G1).

The second stopper 420 is interposed between the stepped part 316 and the second gripping part 330, and may include a second housing 422 which is formed separately from the second gripping part 330, the second core 424 which is formed to be reciprocable in the second housing 422, and a second spring 426 which applies an elastic force to the second core 424.

The second housing 422 may include a second through hole 422a which is formed to penetrate in one direction and a second intersecting hole 422b which intersects with the second through hole 422a.

The second core 424 may be formed to be reciprocable in a third direction and in a fourth direction which is the opposite direction of the third direction along the second intersecting hole 422b.

Further, the second core 424 may include a second communicating hole 424a which is communicable with the second through hole 422a, a second protrusion 424b which protrudes from the second communicating hole 424a and is insertable into any one of the plurality of second grooves (G2), and a second exposing part 424c which is exposed to the outside of the second intersecting hole 422b.

The second spring 426 may be formed of a coil spring which applies an elastic force to the second core 424 in the fourth direction.

Here, the second injection needle guide part 314 is inserted into the second through hole 422a and the second communicating hole 424a, and in this state, in order for the second stopper 420 to be movable along the second injection needle guide part 314, and for the second core 424 to be movable along the second intersecting hole 422b, the second through hole 422a may be formed of a substantially circular hole in which the inner diameter of the second through hole 422a is substantially equal to the outer diameter of the second injection needle guide part 314, and the second communicating hole 424a may be formed of a long hole-shaped hole in which the length of the short axis is substantially equal to the outer diameter of the second injection needle guide part 314 and the length of the long axis is larger than the outer diameter of the second injection needle guide part 314.

Further, the second protrusion 424b may be formed to correspond to the second groove (G2).

Next, the syringe 500 and the second limiting unit 600 according to the present exemplary embodiment will be described with reference to FIGS. 6 and 7.

That is, the syringe 500 may include a hollow barrel 510 having a bore 512 and a plunger 520 which reciprocates along the bore 512 and forms a compression and suction space (V) together with the hollow barrel 510.

Here, a barrel hole 514 which communicates with the compression and suction space (V) may be formed at one end of the hollow barrel 510, and the barrel hole 514 may communicate with or may be blocked from communicating with the pipe (P) which extends from the injection needle 100 by the second limiting unit 600.

The second limiting unit 600 may include a fourth housing 610 which is interposed between the syringe 500 and the pipe (P), a fourth core 620 which is formed to be reciprocable in the fourth housing 610, and a fourth spring 630 which applies an elastic force to the fourth core 620.

The fourth housing 610 may include a fourth through hole 612 which is formed to penetrate in one direction and a fourth intersecting hole 614 which intersects with the fourth through hole 612.

The fourth core 620 may be formed to be reciprocable in a seventh direction and in an eighth direction which is the opposite direction of the seventh direction along the fourth intersecting hole 614.

Further, the fourth core 620 may include a fourth communicating hole 622 which is communicable with the fourth through hole 612 and a fourth exposing part 624 which is exposed to the outside of the fourth intersecting hole 614.

The fourth spring 630 may be formed of a coil spring which applies an elastic force to the fourth core 620 in the eighth direction.

Here, one end 612a of the fourth through hole 612 may communicate with the barrel hole 514; the other end 612b of the fourth through hole 612 may communicate with the pipe (P); when the fourth core 620 moves in the seventh direction, the fourth communicating hole 622 may communicate with the one end 612a of the fourth through hole 612 and the other end 612b of the fourth through hole 612; and when the fourth core 620 moves in the eighth direction, the fourth communicating hole 622 may be formed to be shielded from the one end 612a of the fourth through hole 612 and the other end 612b of the fourth through hole 612.

Meanwhile, referring to FIGS. 1 and 8 to 10, the medical device according to an exemplary embodiment of the present disclosure may further include an incision device which is inserted into the body by using an endoscope.

The incision device may include a knife 700 configured to cut a surgical site, a knife tube 800 which surrounds the knife 700, and a third limiting unit 900 which limits the length of the cutting edge of the knife 700 protruding from the knife tube 800.

The knife 700 may be formed to extend in one direction, one end of the knife 700 may be coupled to a third stopper 920 to be described later, and an incision part (hereinafter, referred to as a cutting edge) configured to cut the surgical site may be formed at the other end of the knife 700.

The knife tube 800 may be formed of a hollow tube, one end of the knife tube 800 may be coupled to a knife guide part 910 to be described later, and a knife gate through which the cutting edge enters and exits may be formed at the other end of the knife tube 800.

The third limiting unit 900 may include the knife guide part 910 which is coupled to the knife tube 800 and extends in one direction and a third stopper 920 which is coupled to the knife 700, is movable along the knife guide part 910, and is fixed to the knife guide part 910 when being positioned at a predetermined position.

The knife guide part 910 may be formed of a tube body which accommodates the knife 700 therein, and a third groove (G3), into which a third protrusion 924b of a third core 924 to be described later is inserted, may be formed in the inner circumferential surface of the knife guide part 910.

A plurality of third grooves (G3) may be formed, and the plurality of third grooves (G3) may be arranged at regular intervals along the extending direction of the knife guide part 910.

Further, each of the plurality of third grooves (G3) may include a third groove first support surface (G31) which supports the third protrusion 924b to be described later at the knife 700 side with respect to the third protrusion 924b to be described later and a third groove second support surface (G32) which supports the third protrusion 924b to be described later at the opposite side of the third groove first support surface (G31) with respect to the third protrusion 924b to be described later.

The third groove first support surface (G31) may be formed perpendicular to the extending direction of the knife guide part 910.

The third groove second support surface (G32) may be formed to be inclined to the extending direction of the knife guide part 910. That is, the third groove second support surface (G32) may be formed to push the third protrusion 924b to be described later to the outside of the third groove (G3) as the third groove second support surface (G32) moves away from the knife 700.

The third stopper 920 may include a third housing 922 which is fastened to the knife 700, a third core 924 which is formed to be reciprocable in the third housing 922, and a third spring 926 which applies an elastic force to the third core 924.

The third housing 922 may include a third through hole 922a which is formed to penetrate in one direction and a third intersecting hole 922b which intersects with the third through hole 922a.

The third core 924 may be formed to be reciprocable in a fifth direction and a sixth direction which is the opposite direction of the fifth direction along the third intersecting hole 922b.

Further, the third core 924 may include a third communicating hole 924a which is communicable with the third through hole 922a, a third protrusion 924b which protrudes from the third communicating hole 924a and is insertable into any one of the plurality of third grooves (G3), and a third exposing part 924c which is exposed to the outside of the third intersecting hole 922b.

The third spring 926 may be formed of a coil spring which applies an elastic force to the third core 924 in the sixth direction.

Here, the knife guide part 910 may be inserted into the third through hole 922a and the third communicating hole 924a, and in this state, in order for the third stopper 920 to be movable along the knife guide part 910, and for the third core 924 to be movable along the third intersecting hole 922b, the third through hole 922a may be formed to have the shape and size corresponding to the knife guide part 910, and the third communicating hole 924a may be formed to have a long hole.

Further, the third protrusion 924b may be formed to correspond to the third groove (G3).

Hereinafter, the operation and effects of the medical device according to the present exemplary embodiment will be described.

That is, the medical device according to the present exemplary embodiment may be injected into the surgical site under the induction of the endoscope to perform tissue collection, medicine injection, and incision in the surgical site.

Specifically, the fine needle aspiration device may be provided in a state where the first gripping part 320 and the second gripping part 330 are spaced apart from each other, such that the injection needle 100 is inserted into the injection needle tube 200.

Further, the injection needle tube 200 into which the injection needle 100 is inserted may penetrate the inside of the endoscope so that the end of the injection needle tube 200 may face the surgical site.

Further, in a state where the first gripping part 320 is gripped with one hand of the operator to be fixed, the second gripping part 330 may be gripped with the other hand of the operator to move toward the first gripping part 320 until the second gripping part 330 is blocked by the second stopper 420. Accordingly, the injection needle 100, which moves together with the second gripping part 330, may have the needlepoint of the injection needle 100 which protrudes from the end the injection needle tube 200, and may be injected into the surgical site.

Here, the protruding length of the injection needle 100 may be adjusted according to a position of the first stopper 410 and a position of the second stopper 420 with respect to the injection needle guide part 310.

Specifically, referring to FIGS. 4 and 5, the position of the first stopper 410 may be determined depending upon which one of the plurality of first grooves (G1) the first protrusion 414b of the first core 414 is inserted into. That is, when an external force by the operator is applied to the first exposing part 414c, the first core 414 may move in the first direction, and the first protrusion 414b may be drawn out from the plurality of first grooves (G1). In this state, the first stopper 410 may move along the first injection needle guide part 312. When the external force applied to the first exposing part 414c is removed after the first stopper 410 is positioned at the desired position on the first injection needle guide part 312, the first core 414 moves in the second direction by the first spring 416, and the first protrusion 414b is inserted into one of the plurality of first grooves (G1), such that the first stopper 410 may be fixed to the first injection needle guide part 312.

Further, the position of the second stopper 420 may be determined depending upon which one of the plurality of second grooves (G2) the second protrusion 424b of the second core 424 is inserted into. That is, when the external force by the operator is applied to the second exposing part 424c, the second core 424 may move in the third direction, and the second protrusion 424b may be drawn out from the plurality of second grooves (G2). In this state, the second stopper 420 may move along the second injection needle guide part 314. When the external force applied to the second exposing part 424c is removed after the second stopper 420 is positioned at the desired position on the second injection needle guide part 314, the second core 424 moves in the fourth direction by the second spring 426, and the second protrusion 424b is inserted into one of the plurality of second grooves (G2), such that the second stopper 420 may be fixed to the second injection needle guide part 314.

However, in the state where the first stopper 410 is fixed to any one position on the first injection needle guide part 312, as the second stopper 420 is positioned adjacent to the stepped part 316 on the second injection needle guide part 314, the stroke of the second gripping part 330 increases, and the stroke of the injection needle 100 which moves together with the second gripping part 330 increases, such that the protruding length of the injection needle 100 may increase.

Further, in the state where the second stopper 420 is fixed to any one position on the second injection needle guide part 314, that is, in the state where the stroke of the injection needle 100 is determined, as the first stopper 410 is positioned adjacent to the stepped part 316 on the first injection needle guide part 312, the injection needle tube 200 which moves together with the first stopper 410 is positioned adjacent to the stepped part 316, such that the protruding length of the injection needle 100 may increase.

Meanwhile, in the state where the injection needle 100 is injected into the surgical site, the syringe 500 (more accurately, the pipe (P)) is connected to the injection needle 100, such that tissue collection or medicine injection may be performed. That is, when the plunger 520 moves backward and negative pressure is applied to the compression and suction space (V) of the syringe, the tissue is sucked from the surgical site through the injection needle 100, the pipe (P), the third stopper 920, and the barrel hole 514, and the sucked tissue may be stored in the compression and suction space (V) of the syringe 500. Alternatively, when the plunger 520 moves forward and positive pressure is applied to the compression and suction space (V) of the syringe 500, the medicine charged in the compression and suction space (V) of the syringe 500 may be injected into the surgical site through the barrel hole 514, the third stopper 920, the pipe (P), and the injection needle 100.

Here, the suction amount and the injection amount by the syringe 500 may be adjusted by the second limiting unit 600.

Specifically, referring to FIGS. 6 and 7, when the external force by the operator is applied to the fourth exposing part 624, the fourth core 620 may move in the seventh direction, and the fourth communicating hole 622 may communicate with the one end 612a of the fourth through hole 612 and the other end 612b of the fourth through hole 612. That is, the one end 612a of the fourth through hole 612 and the other end 612b of the fourth through hole 612 may communicate with each other through the fourth communicating hole 622. Accordingly, the compression and suction space (V) of the syringe 500 may communicate with the injection needle 100 through the barrel hole 514, the one end 612a of the fourth through hole 612, the fourth communicating hole 622, the other end of the fourth through hole 612, and the pipe (P), and the suction amount and the injection amount may increase.

On the other hand, when the external force applied to the fourth exposing part 624 is removed, the fourth core 620 may move in the eighth direction by the fourth spring 630, and the fourth communicating hole 622 may be shielded from the one end 612a of the fourth through hole 612 and the other end 612b of the fourth through hole 612. That is, the communication between the one end 612a of the fourth through hole 612 and the other end 612b of the fourth through hole 612 may be blocked by the fourth core 620. Accordingly, the compression and suction space (V) of the syringe 500 no longer communicates with the injection needle 100, and the suction amount and the injection amount may decrease.

Meanwhile, the incision device may have the cutting edge of the knife 700 which is inserted into the body through the endoscope in the state where the cutting edge of the knife 700 protrudes from the knife tube 800 to cut the surgical site.

Here, the protruding length of the knife 700 may be adjusted according to the position of the third stopper 920 with respect to the knife guide part 910.

Specifically, referring to FIGS. 9 and 10, the position of the third stopper 920 may be determined depending upon which one of the plurality of third grooves (G3) the third protrusion 924b of the third core 924 is inserted into. That is, when the external force by the operator is applied to the third exposing part 924c, the third core 924 may move in the fifth direction, and the third protrusion 924b may be drawn out from the plurality of third grooves (G3). In this state, the third stopper 920 may move along the knife guide part 910. When the external force applied to the third exposing part 924c is removed after the third stopper 920 is positioned at the desired position on the knife guide part 910, the third core 924 moves in the sixth direction by the third spring 926, and the third protrusion 924b is inserted into one of the plurality of third grooves (G3), such that the third stopper 920 may be fixed to the knife guide part 910.

However, in the state where the knife tube 800 is fixed to the knife guide part 910, as the third stopper 920 is positioned adjacent to the knife tube 800 on the knife guide part 910, the knife 700 may move together with the third stopper 920, and the protruding length of the knife 700 may increase.

Here, in the medical device according to the present exemplary embodiment, the first limiting unit 400, the second limiting unit 600, and the third limiting unit 900 are formed so that the limiting functions are released when the external force is applied by the operator and the limiting functions are restored when the external force is removed, thereby enabling a simple and safe operation.

That is, as the first stopper 410 of the first limiting unit 400 which adjusts the protruding length of the injection needle 100 is formed so that the first stopper 410 may move when the operator presses the first exposing part 414c by the hand and the first stopper 410 is automatically fixed by the first spring 416 when the operator releases the finger pressing the first exposing part 414c, the operator may easily operate the first stopper 410 by using only one finger (for example, thumb) of the hand gripping the first gripping part 320 or the first housing 412. Further, upon the operation of the first stopper 410, the fine needle aspiration device may be suppressed from being shaken. That is, unlike in the present exemplary embodiment, if the first exposing part 414c is formed in a pulling and then releasing manner, the operator is required to pull and then release the first exposing part 414c with at least two fingers of the hand after releasing the hand from the first gripping part 320 and the first housing 412, and when the operator pulls and then releases the first exposing part 414c, the first gripping part 320 and the first housing 412 are not supported by the operator's hand, such that the fine needle aspiration device may be shaken, thereby separating the injection needle tube 200 or causing injury around the surgical site. However, in the present exemplary embodiment, the first gripping part 320 or the first housing 412 may be supported by other fingers when the operator presses and then releases the first exposed part 414c with one finger, thereby suppressing the fine needle aspiration device from being shaken.

Further, as the second stopper 420 of the first limiting unit 400 is also formed so that the second stopper 420 may move when the operator presses the second exposing part 424c with the finger and the second stopper 420 is automatically fixed by the second spring 426 when the operator releases the finger pressing the second exposing part 424c, the operator may easily operate the second stopper 420 by using only one finger of the hand which grips the second gripping part 330 or the second housing 422. Further, upon the operation of the second stopper 420, the fine needle aspiration device may be suppressed from being shaken. That is, the second gripping part 330 or the second housing 422 may be supported by other fingers when the operator presses and the releases the second exposing part 424c with one finger, thereby suppressing the fine needle aspiration device from being shaken.

Further, as the second limiting unit 600 which adjusts the suction amount and the injection amount by the syringe 500 is also formed so that the syringe 500 communicates with the injection needle 100 when the operator presses the fourth exposing part 624 with the finger and the communication between the syringe 500 and the injection needle 100 is automatically blocked by the fourth spring 630 when the operator releases the finger pressing the fourth exposing part 624, the operator may easily operate the second limiting unit 600 by using only one finger of the hand which grips the fourth housing 610 or the hollow barrel 510. Further, upon the operation of the second limiting unit 600, the syringe may be suppressed from being shaken. That is, the fourth housing 610 or the hollow barrel 510 is supported with other fingers when the operator presses and then releases the fourth exposing part 624 with one finger, thereby suppressing the syringe 500 from being shaken.

Further, as the third stopper 920 of the third limiting unit 900 which adjusts the protruding length of the knife 700 is also formed so that the third stopper 920 may move when the operator presses the third exposing part 924c with the finger, and the third stopper 920 is automatically fixed by the third spring 926 when the operator releases the finger pressing the third exposing part 924c, the operator may easily operate the third stopper 920 by using only one finger of the hand which grips the third housing 922. Further, upon the operation of the third stopper 920, the incision device may be suppressed from being shaken. That is, the third housing 922 may be supported by other fingers when the operator presses and then releases the third exposing part 924c with one finger, thereby suppressing the incision device from being shaken.

Meanwhile, in the case of the first limiting unit 400, the first groove (G1) of the first stopper 410 and the second groove (G2) of the second stopper 420 may be formed so that the first stopper 410 and the second stopper 420 are difficult to move in a direction in which the first stopper 410 and the second stopper 420 are close to each other and are easy to move in a direction in which the first stopper 410 and the second stopper 420 are close to each other in a state where the first protrusion 414b and the second protrusion 424b are inserted into the first groove (G1) and the second groove (G2), respectively, thereby adjusting the protruding length of the injection needle 100 more simply and safely.

Specifically, as the first groove first support surface (G11) is formed perpendicular to the extending direction of the first injection needle guide part 312, the first groove first support surface (G11) may strongly block the first protrusion 414b even if the first stopper 410 is pushed toward the second stopper 420, thereby preventing the first stopper 410 from moving to be closer to the second stopper 420 than a predetermined position. Further, as the second groove second support surface (G22) is formed perpendicular to the extending direction of the second injection needle guide part 314, the second groove first support surface (G21) may strongly block the second protrusion 424b even if the second stopper 420 is pushed toward the first stopper 410, thereby preventing the second stopper 420 from moving to be closer to the first stopper 410 than a predetermined position. Accordingly, the injection needle 100 may be prevented from protruding further than a predetermined value from the injection needle tube 200, thereby preventing damaging to the tissue.

On the other hand, as the first groove second support surface (G12) is formed to be inclined to the extending direction of the first injection needle guide part 312, the first groove second support surface (G12) may push the first protrusion 414b to the outside of the first groove (G1) when the first stopper 410 is pushed in a direction in which the first stopper 410 moves away from the second stopper 420, thereby making it much easier to move the first stopper 410 in the direction in which the first stopper 410 moves away from the second stopper 420. That is, the operator may easily move the first stopper 410 in the direction in which the first stopper 410 moves away from the second stopper 420 only by pulling the first stopper 410 in the direction in which the first stopper 410 moves away from the second stopper 420 by slightly pressing a first button part or even without pressing the first button part. Further, as the second groove first support surface (G21) is formed to be inclined to the extending direction of the second injection needle guide part 314, the second groove second support surface (G22) may push the second protrusion 424b to the outside of the second groove (G2) when the second stopper 420 is pushed in the direction in which the second stopper 420 moves away from the first stopper 410, thereby making it much easier to move the second stopper 420 in the direction in which the second stopper 420 moves away from the first stopper 410. That is, the operator may easily move the second stopper 420 in the direction in which the second stopper 420 moves away from the first stopper 410 only by pulling the second stopper 420 in the direction in which the second stopper 420 moves away from the first stopper 410 by slightly pressing a second button part or even without pressing the second button part. Here, when the first stopper 410 and the second stopper 420 move in the direction in which the first stopper 410 and the second stopper 420 move away from each other, the protruding length of the injection needle 100 decreases, such that there is no risk that the injection needle 100 damages the tissue and thus, there is no problem even if the first stopper 410 and the second stopper 420 are formed to easily move in the direction in which the first stopper 410 and the second stopper 420 move away from each other.

Meanwhile, in the case of the third limiting unit 900, similar to the first limiting unit 400, the third groove (G3) of the third stopper 920 is formed so that the third stopper 920 is difficult to move toward the knife 700 and is easy to move to the opposite side of the knife 700 (hereinafter, the opposite direction of the knife 700) with respect to the third stopper 920 in a state where the third protrusion 924b is inserted into the third groove (G3), thereby adjusting the protruding length of the knife 700 more simply and safely.

Specifically, as the third groove first support surface (G31) is formed perpendicular to the extending direction of the knife guide part 910, the third groove first support surface (G31) may strongly block the third protrusion 924b even if the third stopper 920 is pushed toward the knife 700, thereby preventing the third stopper 920 from moving to be closer to the knife 700 than a predetermined position. Accordingly, the knife 700 may be prevented from protruding further than a predetermined value from the knife tube 800, thereby preventing damage to the tissue.

On the other hand, as the third groove second support surface (G32) is formed to be inclined to the extending direction of the knife guide part 910, the third groove second support surface (G32) may push the third protrusion 924b to the outside of the third groove (G3) when the third stopper 920 is pushed in the opposite direction of the knife 700, thereby making it much easier to move the third stopper 920 in the opposite direction of the knife 700. That is, the operator may easily move the third stopper 920 in the opposite direction of the knife 700 only by pulling the third stopper 920 in the opposite direction of the knife 700 by slightly pressing a third button part or even without pressing the third button part. Here, when the third stopper 920 moves in the opposite direction of the knife 700, the protruding length of the knife 700 decreases, such that there is no risk that the knife 700 damages the tissue and thus, there is no problem even if the third stopper 920 is formed to easily move in the opposite direction of the knife 700.

INDUSTRIAL APPLICABILITY

The present disclosure provides the medical device which may be inserted into the body by using the endoscope to perform the treatment such as tissue collection and medicine injection.

The invention claimed is:

1. A medical system comprising:
a fine needle aspiration device and an incision device which are inserted into a body by using an endoscope,
wherein the fine needle aspiration device comprises:
an injection needle which is injected into a surgical site;
an injection needle tube which surrounds the injection needle;
a first limiting unit which limits a length of a needlepoint of the injection needle protruding from the injection needle tube;
a syringe which is connected to the injection needle for tissue collection and medicine injection; and
a second limiting unit which limits injection flow between the injection needle and the syringe by actuation of an exposing part that allows the injection flow when actuated and prevents the injection flow when not actuated,
wherein the incision device comprises:
a knife configured to cut the surgical site;
a knife tube which surrounds the knife; and
a third limiting unit which limits a length of a cutting edge of the knife protruding from the knife tube, and
wherein at least one of the first limiting unit, the second limiting unit, and the third limiting unit is formed so that a limiting function is released when an external force is applied by an operator and the limiting function is restored when the external force is removed,
wherein the fine needle aspiration device further comprises an injection needle operating mechanism which moves the injection needle so that the needlepoint of the injection needle protrudes from the injection needle tube or is inserted into the injection needle tube,
wherein the injection needle operating mechanism comprises:
a first injection needle guide part extending in one direction and a second injection needle guide part extending in an opposite direction of the first injection needle guide part;
a first gripping part which is coupled to the injection needle tube and is movable along the first injection needle guide part; and
a second gripping part which is coupled to the injection needle and is movable along the second injection needle guide part, and
wherein the first limiting unit comprises:
a first stopper which fixes the first gripping part to the first injection needle guide part; and
a second stopper which prevents the second gripping part from being closer to the first gripping part than a predetermined position.

2. The medical system of claim 1, wherein the first stopper comprises:
a first housing which has a first through hole formed to penetrate in one direction and a first intersecting hole intersecting with the first through hole and is formed integrally with the first gripping part;
a first core which is provided to be reciprocable in a first direction and a second direction which is the opposite direction of the first direction along the first intersecting hole and has a first communicating hole which is communicable with the first through hole; and
a first spring which applies an elastic force to the first core in the second direction, and
wherein the first injection needle guide part is inserted into the first through hole and the first communicating hole.

3. The medical system of claim 2,
wherein the first injection needle guide part is formed with a plurality of first grooves along the extending direction of the first injection needle guide part,
wherein the first core comprises a first protrusion which protrudes from the first communicating hole and is insertable into any one of the plurality of first grooves and a first exposing part which is exposed to the outside of the first intersecting hole,
wherein when the external force is applied to the first exposing part, the first core moves in the first direction by the external force, and the first protrusion is drawn out from the plurality of first grooves such that the first gripping part and the first stopper are movable along the first injection needle guide part, and
wherein when the external force is removed, the first core moves in the second direction by the first spring, and the first protrusion is inserted into any one of the plurality of first grooves, such that the first gripping part and the first stopper are fixed to the first injection needle guide part.

4. The medical system of claim 3,
wherein the plurality of first grooves comprises:
a first groove first support surface which supports the first protrusion at the second gripping part side with respect to the first protrusion; and a first groove second support surface which supports the first protrusion at the opposite side of the first groove first support surface with respect to the first protrusion, wherein the first groove first support surface is formed perpendicular to the extending direction of the first injection needle guide part, and wherein the first groove second support surface is formed to be inclined to the extending direction of the first injection needle guide part so as to push the first protrusion to the outside of the first groove as the first groove second support surface moves away from the second gripping part.

5. The medical system of claim 1, wherein the second stopper comprises:
a second housing which has a second through hole formed to penetrate in one direction and a second intersecting hole intersecting with the second through hole and is provided between the first gripping part and the second gripping part;
a second core which is provided to be reciprocable in a third direction and a fourth direction which is the opposite direction of the third direction along the second intersecting hole and has a second communicating hole which is communicable with the second through hole; and
a second spring which applies an elastic force to the second core in the fourth direction, and
wherein the second injection needle guide part is inserted into the second through hole and the second communicating hole.

6. The medical system of claim 5,
wherein the second injection needle guide part is formed with a plurality of second grooves along the extending direction of the second injection needle guide part,
wherein the second core comprises a second protrusion which protrudes from the second communicating hole and is insertable into any one of the plurality of second grooves and a second exposing part which is exposed to the outside of the second intersecting hole,
wherein when the external force is applied to the second exposing part, the second core moves in the third direction by the external force, and the second protrusion is drawn out from the plurality of second grooves, such that the second stopper is movable along the second injection needle guide part, and
wherein when the external force is removed, the second core moves in the fourth direction by the second spring, and the second protrusion is inserted into any one of the plurality of second grooves such that the second stopper is fixed to the second injection needle guide part.

7. The medical system of claim 6,
wherein the second gripping part is movable along the second injection needle guide part separately from the second stopper, and
wherein the second gripping part moves toward the first gripping part and then is blocked by the second stopper, thereby preventing the second gripping part from being closer to the first gripping part than a predetermined position.

8. The medical system of claim 6,
wherein the plurality of second grooves comprises:
a second groove first support surface which supports the second protrusion at the first gripping part side with respect to the second protrusion; and
a second groove second support surface which supports the second protrusion at the opposite side of the second groove first support surface with respect to the second protrusion, wherein the second groove first support surface is formed perpendicular to the extending direction of the second injection needle guide part, and wherein the second groove second support surface is formed to be inclined to the extending direction of the second injection needle guide part so as to push the second protrusion to the outside of the second groove as the second groove second support surface moves away from the first gripping part.

9. A medical system comprising:
a fine needle aspiration device and an incision device which are inserted into a body by using an endoscope,
wherein the fine needle aspiration device comprises:
an injection needle which is injected into a surgical site;
an injection needle tube which surrounds the injection needle;
a first limiting unit which limits a length of a needlepoint of the injection needle protruding from the injection needle tube;
a syringe which is connected to the injection needle for tissue collection and medicine injection; and
a second limiting unit which limits injection flow between the injection needle and the syringe by actuation of an exposing part that allows the injection flow when actuated and prevents the injection flow when not actuated,
wherein the incision device comprises:
a knife configured to cut the surgical site;
a knife tube which surrounds the knife; and
a third limiting unit which limits a length of a cutting edge of the knife protruding from the knife tube, and
wherein at least one of the first limiting unit, the second limiting unit, and the third limiting unit is formed so that a limiting function is released when an external force is applied by an operator and the limiting function is restored when the external force is removed,
wherein the third limiting unit comprises:
a knife guide part which is coupled to the knife tube and extends in one direction; and
a third stopper which is coupled to the knife, is movable along the knife guide part, and is fixed to the knife guide part when being positioned at a predetermined position.

10. The medical system of claim 9,
wherein the third stopper comprises:
a third housing which has a third through hole formed to penetrate in one direction and a third intersecting hole intersecting with the third through hole and is coupled to the knife;
a third core which is provided to be reciprocable in a fifth direction and a sixth direction which is the opposite direction of the fifth direction along the third intersecting hole and has a third communicating hole which is communicable with the third through hole; and
a third spring which applies an elastic force to the third core in the sixth direction, and
wherein the knife guide part is inserted into the third through hole and the third communicating hole.

11. The medical system of claim 10,
wherein the knife guide part is formed with a plurality of third grooves along the extending direction of the knife guide part, wherein the third core comprises a third protrusion which protrudes from the third communicating hole and is insertable into any one of the plurality of third grooves and a third exposing part which is exposed to the outside of the third intersecting hole, wherein when the external force is applied to the third exposing part, the third core moves in the fifth direction by the external force, and the third protrusion is drawn out from the plurality of third grooves, such that the third stopper is movable along the knife guide part, and wherein when the external force is removed, the third core moves in the sixth direction by the third spring, and the third protrusion is inserted into any one of the plurality of third grooves, such that the third stopper is fixed to the knife guide part.

12. The medical system of claim 11, wherein the plurality of third grooves comprises:

a third groove first support surface which supports the third protrusion at the knife side with respect to the third protrusion; and a third groove second support surface which supports the third protrusion at the opposite side of the third groove first support surface with respect to the third protrusion, wherein the third groove first support surface is formed perpendicular to the extending direction of the knife guide part, and wherein the third groove second support surface is formed to be inclined to the extending direction of the knife guide part so as to push the third protrusion to the outside of the third groove as the third groove second support surface moves away from the knife.

13. A medical system comprising:

a fine needle aspiration device and an incision device which are inserted into a body by using an endoscope, wherein the fine needle aspiration device comprises:

an injection needle which is injected into a surgical site;

an injection needle tube which surrounds the injection needle;

a first limiting unit which limits a length of a needlepoint of the injection needle protruding from the injection needle tube;

a syringe which is connected to the injection needle for tissue collection and medicine injection; and a second limiting unit which limits injection flow between the injection needle and the syringe by actuation of an exposing part that allows the injection flow when actuated and prevents the injection flow when not actuated, wherein the incision device comprises:

a knife configured to cut the surgical site;

a knife tube which surrounds the knife; and a third limiting unit which limits a length of a cutting edge of the knife protruding from the knife tube, and wherein at least one of the first limiting unit, the second limiting unit, and the third limiting unit is formed so that a limiting function is released when an external force is applied by an operator and the limiting function is restored when the external force is removed, wherein the syringe comprises:

a hollow barrel which has a bore; and a plunger which reciprocates along the bore, wherein the second limiting unit comprises:

a fourth housing which has a fourth through hole formed to penetrate in one direction and a fourth intersecting hole intersecting with the fourth through hole;

a fourth core which is provided to be reciprocable in a seventh direction and an eighth direction which is the opposite direction of the seventh direction along the fourth intersecting hole and has a fourth communicating hole which is communicable with the fourth through hole; and a fourth spring which applies an elastic force to the fourth core in the eighth direction, wherein one end of the fourth through hole communicates with the syringe, and wherein the other end of the fourth through hole communicates with the injection needle.

14. The medical system of claim 13, wherein the fourth core comprises a fourth exposing part which is exposed to the outside of the fourth intersecting hole, wherein when the external force is applied to the fourth exposing part, the fourth core moves in the seventh direction by the external force, and the fourth communicating hole communicates with the fourth through hole, such that the syringe communicates with the injection needle through the fourth through hole and the fourth communicating hole, and wherein when the external force is removed, the fourth core moves in the eighth direction by the fourth spring, and the fourth communicating hole is shielded from the fourth through hole, thereby blocking the communication between the syringe and the injection needle.

* * * * *